(12) United States Patent
Bae

(10) Patent No.: US 10,076,488 B2
(45) Date of Patent: Sep. 18, 2018

(54) LONG-LASTING POWDER ESSENCE COMPOSITION WITH IMPROVED COLORING AND SKIN FEELING AND PREPARATION METHOD THEREOF

(71) Applicant: C&C INTERNATIONAL CO., LTD., Gyeonggi-do (KR)

(72) Inventor: Eun-chul Bae, Gyeonggi-do (KR)

(73) Assignee: C&C INTERNATIONAL CO., LTD., Gyeonggi-do (KR)

( * ) Notice: Subject to any disclaimer, the term of this patent is extended or adjusted under 35 U.S.C. 154(b) by 174 days.

(21) Appl. No.: 15/292,188

(22) Filed: Oct. 13, 2016

(65) Prior Publication Data

US 2017/0231895 A1  Aug. 17, 2017

(30) Foreign Application Priority Data

Oct. 23, 2015 (KR) .......... 10-2015-0147970

(51) Int. Cl.
| | | |
|---|---|---|
| *A61K 8/02* | (2006.01) | |
| *A61K 8/891* | (2006.01) | |
| *A61K 8/25* | (2006.01) | |
| *A61K 8/29* | (2006.01) | |
| *A61K 8/31* | (2006.01) | |
| *A61K 8/34* | (2006.01) | |
| *A61K 8/37* | (2006.01) | |
| *A61Q 1/12* | (2006.01) | |
| *A61K 8/60* | (2006.01) | |
| *A61K 8/65* | (2006.01) | |
| *A61K 8/73* | (2006.01) | |
| *A61K 8/06* | (2006.01) | |
| *A61K 8/44* | (2006.01) | |
| *A61Q 1/04* | (2006.01) | |
| *A61Q 1/08* | (2006.01) | |

(52) U.S. Cl.
CPC .............. *A61K 8/891* (2013.01); *A61K 8/064* (2013.01); *A61K 8/25* (2013.01); *A61K 8/29* (2013.01); *A61K 8/31* (2013.01); *A61K 8/34* (2013.01); *A61K 8/345* (2013.01); *A61K 8/37* (2013.01); *A61K 8/44* (2013.01); *A61K 8/60* (2013.01); *A61K 8/602* (2013.01); *A61K 8/606* (2013.01); *A61K 8/65* (2013.01); *A61K 8/732* (2013.01); *A61Q 1/04* (2013.01); *A61Q 1/08* (2013.01); *A61Q 1/12* (2013.01); *A61K 2800/43* (2013.01); *H05K 999/99* (2013.01)

(58) Field of Classification Search
CPC .... A61K 2300/00; A61K 36/67; A61K 36/81; A61K 2800/872; A61K 31/4155; A61K 8/02; A61K 8/064; A61K 8/72; A61K 8/732; A61K 9/0014; A61K 2800/31; A61K 2800/43; A61K 2800/5426; A61K 2800/594; A61K 2800/782; A61K 31/11; A61K 31/16; A61K 47/22; A61K 8/0212; A61K 8/0229; A61K 8/062; A61K 8/14; A61K 8/25; A61K 8/31; A61K 8/65; A61K 8/37; A61K 8/44; A61K 8/498; A61K 8/60
USPC ........................................ 424/401
See application file for complete search history.

(56) References Cited

U.S. PATENT DOCUMENTS

2008/0241084 A1* 10/2008 Siddiqui .................. A61K 8/97
424/62

* cited by examiner

*Primary Examiner* — Nannette Holloman
(74) *Attorney, Agent, or Firm* — Luoh J. Wu; Continent Patent Office LLP

(57) ABSTRACT

The present invention relates to a long-lasting powder essence composition with improved coloring and skin feeling and its preparation method. The powder essence composition is a high-fitting coloring powder not likely to smear or wear off. The composition turns into liquid the moment it is rubbed on the skin to offer a natural color tone like water color, keeps the color clear without getting cakey even when it is reapplied multiple times, and delivers a clearer color as it glides on the skin to break powder and water particles. The powder essence composition according to the present invention is also a powder emulsion, which makes the skin feel light and hydrated rather than sticky or stuffy when applied to the skin and stays long due to its water-resistant function. In addition, the powder essence composition according to the present invention contains different functional moisturizing agents to provide plenty of nourishment when applied to the skin. The composition makes the skin feel fresh and hydrated rather than stuffy or heavy, lightly sinks into the skin like nothing is applied on the skin, to display a strong tint function, stays long just with one touch and has a good water-resistant effect, so it does not bleed when in contact with water.

5 Claims, 2 Drawing Sheets

LONG-LASTING POWDER ESSENCE COMPOSITION WITH IMPROVED COLORING AND SKIN FEELING AND PREPARATION METHOD THEREOF

RELATED APPLICATION

The present application claims a priority benefit to Korean Patent Application No. 10-2015-0147970 filed on Oct. 23, 2016, which is incorporated herein by reference.

TECHNICAL FIELD

The present invention relates to a long-lasting powder essence composition with improved coloring and skin feeling and its preparation method. More particularly, the present invention relates to a water-resistant powder essence composition and its preparation method, where the powder essence composition takes the form of powder before use and turns into liquid the moment it is rubbed on the skin to offer a natural color tone like water color, so it does not get cakey feeling on the skin even when it is reapplied multiple times, but keeps a clear color for a long time and helps the skin feel light and hydrated rather than sticky or stuffy.

BACKGROUND ART

Powder essence, also referred to as "water powder", "liquid marbles" or "dry water", means water-in-powder type functional cosmetic preparation in the powder form that contains different moisturizing and functional ingredients.

Powder essence, normally in the form of powder, turns into liquid when rubbed on the skin of hands or face and offers the function to protect unstable functional ingredients from being broken and help them efficiently absorbed or transferred into the skin when in use.

The following patent document 1 discloses a water-in-silicone emulsion type makeup cosmetic composition comprising 0.1 to 5 wt. % of silica dimethyl silylate, 9.9 to 55 wt. % of a silicone-based oil, 2 to 25 wt. % of a pigment, and 15 to 89 wt. % of water. This cosmetic composition delivers unclear color when applied on lips or cheeks and creates a little bit poor skin feeling as it feels heavy and cakey on the skin.

In addition, the following patent document 2 specifies a water-resistant powder type cosmetic composition comprising 2 to 15 wt. % of spherical porous powder, 1 to 10 wt. % of silica silylate, 10 to 20 wt. % of pigment or mica, 5 to 15 wt. % of an oil component, 1 to 10 wt. % of a moisturizing component, and 20 to 80 wt. % of purified water, with respect to the total weight of the powder type cosmetic composition. This cosmetic composition fails to offer a natural color tone like water color even with the addition of different pigments and delivers a sticky and stuffy feeling on the skin, leaving a lot to be desired, while most of all customers prefer feeling light on the skin like wearing nothing at all as well as having the skin feel light and hydrated.

Accordingly, there is a demand for development of a powder emulsion type essence composition that does not feel sticky, stuffy or heavy, but sinks into the skin lightly, making the user feel like wearing nothing at all, displays a strong tint function to stay on the skin for a long period of time just with no one touch, and does not get cakey even when it is reapplied multiple times, ending up having a clear and light tone of color stay without change and delivering a natural color tone like water color.

PRIOR ART

Patent Documents

Patent Document 1: KR Laid-open Patent Publication No. 10-2008-0094388, filled on Oct. 23, 2008
Patent Document 2: KR Registered Patent Publication No. 10-1023535, filled on Mar. 11, 2011

DISCLOSURE OF INVENTION

In an attempt to solve the problems with the prior art, the inventors of the present invention have found out the fact that it is possible to prepare an innovative water-resistant emulsion type powder essence composition using silica dimethicone silylate, water, glycerine, phenoxy ethanol, glycosyl trehalose, hydrogenated starch hydrolysate, methylparaben, silica, methicone, and squalane, which essence composition delivers a clear color, with a natural color tone like water color, keeps the color clear for a long period of time, and makes the skin feel light and hydrated rather than sticky or cakey, thereby completing the present invention.

It is therefore a first object of the present invention to provide a powder essence composition with good coloring performance and color retention and dramatically improved skin feeling.

It is a second object of the present invention to provide a method for preparing a powder essence composition with good coloring performance and color retention and dramatically improved skin feeling.

In accordance with one embodiment of the present invention for achieving the first object of the present invention, there is provided a long-lasting powder essence composition with improved coloring and skin feeling that comprises: 5 to 7 parts by weight of silica dimethicone silylate, 50 to 80 parts by weight of water, 1 to 10 parts by weight of glycerine, 0.001 to 0.003 part by weight of phenoxy ethanol, 0.5 to 3 parts by weight of glycosyl trehalose, 0.3 to 2 parts by weight of hydrogenated starch hydrolysate, 0.1 to 0.5 part by weight of methylparaben, 1 to 5 parts by weight of silica, 0.03 to 0.2 part by weight of methicone, 1 to 3 parts by weight of squalane, and 5 to 10 parts by weight of a pigment.

In accordance with another embodiment of the present invention, the long-lasting powder essence composition with improved coloring and skin feeling further comprises: 1 to 5 parts by weight of betaine, 1 to 5 parts by weight of arbutin, 0.01 to 0.1 part by weight of adenosine, and 0.5 to 5 parts by weight of trehalose.

In accordance with still another embodiment of the present invention, the long-lasting powder essence composition with improved coloring and skin feeling further comprises: 1 to 3 parts by weight of butylene glycol and 1 to 3 parts by weight of hydrolyzed collagen.

In accordance with one embodiment of the present invention for achieving the second object of the present invention, there is provided a method for preparing a long-lasting powder essence composition with improved coloring and skin feeling that comprises: (1) adding 5 to 7 parts by weight of silica dimethicone silylate to a preparation container and stirring; (2) adding 50 to 80 parts by weight of water, 1 to 10 parts by weight of glycerine, 0.001 to 0.003 part by weight of phenoxy ethanol, 0.5 to 3 parts by weight of glycosyl trehalose, 0.3 to 2 parts by weight of hydrogenated starch hydrolysate, and 0.1 to 0.5 part by weight of methylparaben, and dissolving under agitation to prepare a solution; (3) sufficiently mixing the solution with the stirred silica dimethicone silylate so that the solution is impregnated with the silica dimethicone silylate, thereby preparing a mixture; (4) adding 1 to 5 parts by weight of silica and 0.03 to 0.2 part by weight of methicone to the mixture, adding 1 to 3 parts by weight of squalane to the mixture including silica and methicone, and stirring; and (5) adding 5 to 10 parts by weight of a pigment and stirring.

In accordance with another embodiment of the present invention, the step (2) further includes adding 1 to 5 parts by weight of betaine, 1 to 5 parts by weight of arbutin, 0.01 to 0.1 part by weight of adenosine, 0.5 to 5 parts by weight of trehalose, 1 to 3 parts by weight of butylene glycol, and 1 to 3 parts by weight of hydrolyzed collagen, and dissolving under agitation.

EFFECTS OF INVENTION

The powder essence composition according to the present invention is a high-fitting [밀착형] coloring powder not likely to smear or wear off. The composition turns into liquid the moment it is rubbed on the skin to offer a natural color tone like water color, keeps the color clear without getting cakey even when it is reapplied multiple times, and delivers a clearer color as it glides on the skin to break powder and water particles. Further, the powder essence composition according to the present invention is a powder emulsion, which makes the skin feel light and hydrated rather than sticky or stuffy when applied to the skin and stays long due to its water-resistant function. In addition, the powder essence composition according to the present invention contains different functional moisturizing agents to provide plenty of nourishment when applied to the skin. As the water capsules pop and turn into water form upon the powder type (or water-in-powder) essence gliding on the skin, the composition makes the skin feel fresh and hydrated rather than stuffy or heavy, lightly sinks into the skin like nothing is applied on the skin, to display a strong tint function, stays long just with one touch and has a good water-resistant effect, so it does not bleed when in contact with water.

BEST MODES FOR CARRYING OUT THE INVENTION

Figure 1:
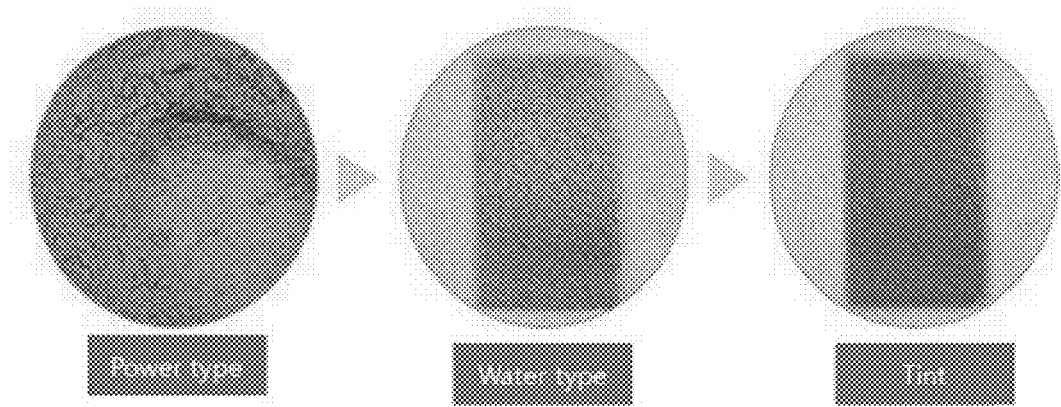
FIG. 1 is an image showing that the composition according to one embodiment of the present invention turns into another form to offer a clear and bright tint on the skin.
Figure 2:
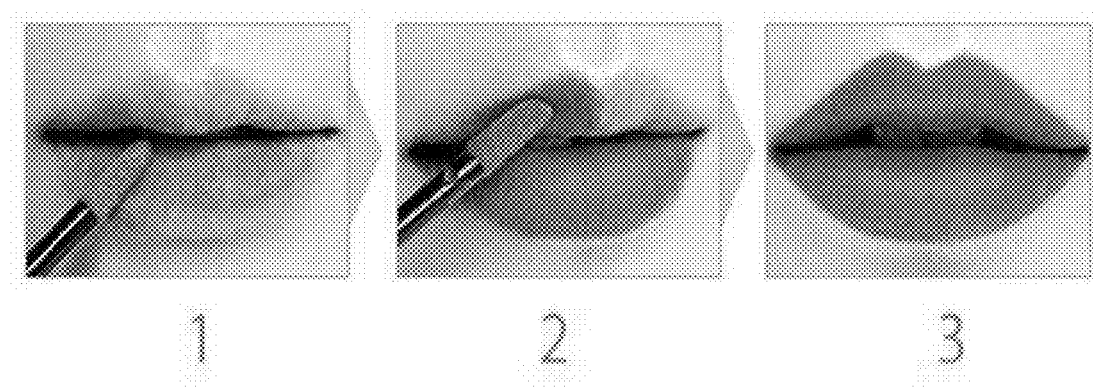
FIG. 2 is an image showing that the composition according to one embodiment of the present invention applied to a lip can deliver clear color and line of a downy lip.
Figure 3:
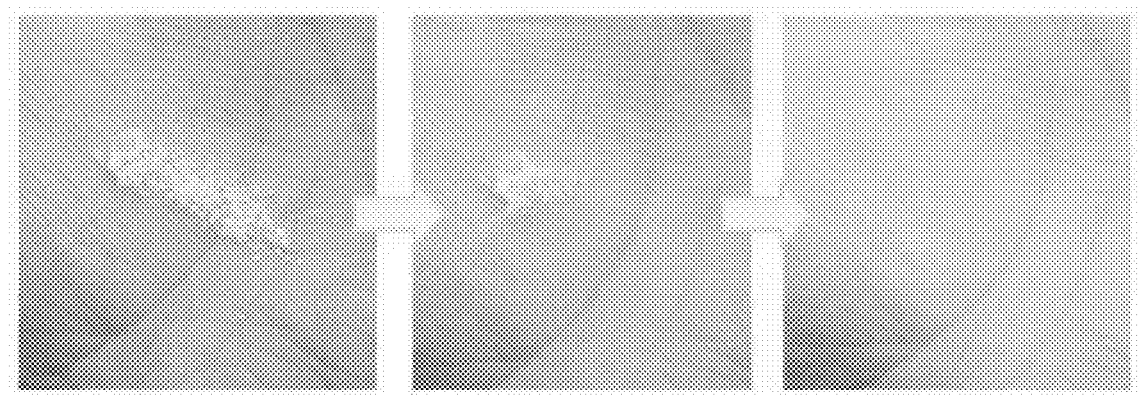
FIG. 3 is an image showing that the composition according to one embodiment of the present invention applied to a palm lightly sinks into the skin, so it does not make the palm feel sticky or look glistening.
Figure 4:
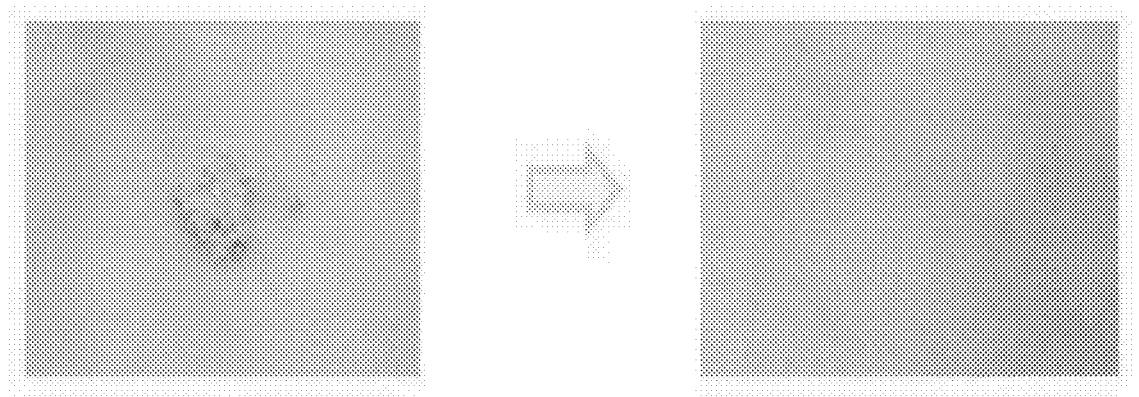
FIG. 4 is an image showing that the composition according to one embodiment of the present invention applied to a face delivers a light and clear color and offers a very natural color tone like water color.

Prior to the further specific description of the present invention, it should be understood that the terms used in this disclosure and the claims are not to be confined to the common or dictionary meanings but interpreted to have meanings and concepts coinciding with the technical conceptions of the present invention on the basis of the principle that the concepts of the terms can be properly defined for the sake of the best explanation of the present invention. Therefore, specific details disclosed herein are not to be interpreted as representing all the technical conceptions of the present invention but given as a preferred example of the present invention. Obviously, many equivalents and variations that may replace the embodiments given herein are possible in the light of the teaching of the present disclosure.

Hereinafter, the present invention will be described in further detail with reference to the preferred embodiments in order for those skilled in the art to embody the present invention with ease. In the following description of the present invention, a detailed description of known functions and configurations incorporated herein will be omitted when it may make the subject matter of the present invention rather unclear.

The present invention is directed to a long-lasting powder essence composition with improved coloring and skin feeling and its preparation method. More particularly, the present invention is directed to a water-resistant powder essence composition and its preparation method, where the powder essence composition takes the form of powder before use and turns into liquid the moment it is rubbed on the skin to offer a natural color tone like water color, so it does not get a cakey feeling on the skin even when it is reapplied multiple times, but keeps a clear color for a long time and helps the skin feel light and hydrated rather than sticky or stuffy.

The powder essence composition according to one embodiment of the present invention comprises silica dimethicone silylate, water, glycerin, phenoxy ethanol, glycosyl trehalose, hydrogenated starch hydrolysate, methylparaben, silica, methicone, squalane, and a pigment.

Silica dimethicone silylate, an ingredient for powder essence, forms an interface with water to provide an emulsion structure. Also, silica dimethicone silylate acts as a bulking agent in the powder essence composition of the present invention. The powder essence composition contains 5 to 7 parts by weight of silica dimethicone silylate. When the content of silica dimethicone silylate is less than 5 parts by weight, it is hard to form a powder emulsion. When the content of silica dimethicone silylate is greater than 7 parts by weight, it results in dry texture.

Water displays the function of a solvent in the powder essence composition of the present invention. Preferably, the water is deionized (DI) water. Water is used in an amount of 50 to 80 parts by weight. When the content of water is less than 50 parts by weight, the other components included in the composition do not dissolve sufficiently, or the powder essence composition deteriorates in terms of the skin feeling. When the content of water is greater than 80 parts by weight, water is likely to form a precipitate instead of emulsion.

Glycerin serves as a skin-conditioning agent and contained in an amount of 1 to 10 parts by weight. When the content of glycerin is less than 1 part by weight, the powder essence composition displays deterioration in the moisturizing effect, so it makes the skin feel dry fast when it is applied to the skin. When the content of glycerin is greater than 10 parts by weight, it is uneconomical.

Phenoxy ethanol has the function of a preservative and serves to prevent the powder essence composition of the present invention from denaturation or changing in characteristics of the functional ingredients during a long-term storage. The phenoxy ethanol is contained in an amount of 0.001 to 0.03 part by weight. When the content of phenoxy ethanol is less than 0.01 part by weight, the powder essence composition is likely to deteriorate in the preservation. When the content of phenoxy ethanol is greater than 0.03 part by weight, the powder essence possibly can be potentially toxic.

Glycosyl trehalose displays the function of a skin protectant and serves to protect the skin against UV rays, polluted air, etc. The glycosyl trehalose is contained in an amount of 0.5 to 3 parts by weight. When the content of glycosyl trehalose is less than 0.5 part by weight, the powder essence composition has deterioration in the skin-protecting function. When the content of glycosyl trehalose is greater than 3 parts by weight, it is uneconomical.

Hydrogenated starch hydrolysate also displays the function of a skin protectant and serves to protect the skin against UV rays, polluted air, etc. The hydrogenated starch hydrolysate is contained in an amount of 0.3 to 2 parts by weight. When the content of hydrogenated starch hydrolysate is less than 0.3 part by weight, the powder essence composition has deterioration in the skin-protecting function. When the content of hydrogenated starch hydrolysate is greater than 2 parts by weight, it is uneconomical.

Like phenoxy ethanol, methylparaben functions to enhance the preservative function of the powder essence composition. The methylparaben is contained in an amount of 0.1 to 0.5 part by weight. When the content of methylparaben is less than 0.1 part by weight, the powder essence composition deteriorates in the preservative function during the storage. When the content of methylparaben is greater than 0.5 part by weight, the powder essence composition can be potentially toxic.

As described above, the powder essence composition of the present invention has different moisturizing agents to provide enough nourishment for the skin and contains antioxidants and preservatives to prevent the contents from decaying.

In addition, the composition of the present invention may further comprise 1 to 5 parts by weight of betaine anhydrous, 1 to 5 parts by weight of arbutin, 0.01 to 0.1 part by weight of adenosine, and 0.5 to 5 parts by weight of trehalose. Betaine and trehalose play as a skin-conditioning agent, and arbutin displays skin-whitening and antioxidant effects. And, adenosine is effective against wrinkles.

In addition, the composition of the present invention may further comprise 1 to 3 parts by weight of butylene glycol and 1 to 3 parts by weight of hydrolyzed collagen. Both butylene glycol and hydrolyzed collagen function as a skin-conditioning agent. The butylene glycol and hydrolyzed collagen as used herein may be available from pigskin collagen.

Silica, together with silica dimethicone silylate, acts as a bulking agent for the powder essence composition of the present invention and is useful as a sebum control ingredient highly effective in sebum control that helps adsorb sebum and minimize pores to improve the skin texture. Further, silica serves as an exfoliating agent for skin and fills in the gaps such as wrinkles to make the skin look smooth. In the composition of the present invention, silica is contained in an amount of 1 to 5 parts by weight. When the content of silica is less than 1 part by weight, the composition deteriorates in the wrinkle-reducing function or the composition bulking effect.

When the content of silica is greater than 5 parts by weight, the powder composition cannot make the skin feel light or hydrated as usual and deteriorates in the skin feeling, ending up having stiff texture.

Methicone functions as a skin-conditioning agent. Due to its low air permeability and high water-repellency, it serves to increases skin moisturization, spreadability and absorbability of the powder essence composition according to the present invention. In particular, methicone together with silica helps pigments disperse evenly in the case that the powder has large particles. Further, methicone forms a thin film on the skin to prevent the color retention of the powder essence composition from reducing due to sweat, oil, water, etc. The methicone is contained in an amount of 0.03 to 0.2 part by weight. When the content of methicone is less than 0.03 part by weight, the powder essence composition has deterioration in the skin moisturization, spreadability and absorbability, or deterioration in the even dispersability of pigments. When the content of methicone is greater than 0.2 part by weight, it is likely to inhibit the secretion of water or sweat from the skin.

Squalane, as a skin-conditioning agent, displays a function to keep moisture from evaporating, so it prevents water evaporation when the powder essence composition is applied to the skin. Further, squalane forms a coating of the emulsified powder on the skin to provide soft texture for skin. The squalane is contained in an amount of 1 to 3 parts by weight. When the content of squalane is less than 1 part by weight, the composition deteriorates in the effect to keep moisture from evaporating and thus fails to provide soft texture for skin. When the content of squalane is greater than 3 parts by weight, the emulsified particles break, so water may collect.

The pigment is to deliver different colors for the powder essence composition. The pigment as used herein may be any type of pigment normally available in the cosmetic compositions. The pigment is contained in an amount of 5 to 10 parts by weight. When the content of the pigment is less than 5 parts by weight, it reduces the coloring effect. When the content of the pigment is greater than 10 parts by weight, the contents of the other effective ingredients can be decreased relatively. When the powder essence composition of the present invention glides on the skin, the essence particles pop and the pigment contained in the powder essence imparts color to the skin.

Hereinafter, a detailed description will be given as to a method for preparing the powder essence composition according to the present invention.

Firstly, 5 to 7 parts by weight of silica dimethicone silylate is put into a preparation container and stirred with an Agi-mixer or the like, in step (1). The step (1) is performed at the room temperature until the silica dimethicone silylate is sufficiently agitated.

Then, 50 to 80 parts by weight of water, 1 to 10 parts by weight of glycerine, 0.001 to 0.003 part by weight of phenoxy ethanol, 0.5 to 3 parts by weight of glycosyl trehalose, 0.3 to 2 parts by weight of hydrogenated starch hydrolysate, and 0.1 to 0.5 part by weight of methylparaben are added and dissolved under agitation to prepare a solution, in step (2).

In the step (2), 1 to 5 parts by weight of betaine, 1 to 5 parts by weight of arbutin, 0.01 to 0.1 part by weight of adenosine, 0.5 to 5 parts by weight of trehalose, 1 to 3 parts by weight of butylene glycol, and 1 to 3 parts by weight of butylene glycol and 1 to 3 parts by weight of hydrolyzed collagen may be further added.

Subsequently, the solution is mixed with the stirred silica dimethicone silylate using a mixer or the like so that it is completely impregnated with the silica dimethicone silylate, thereby preparing a mixture, in step (3).

Subsequently, 1 to 5 parts by weight of silica and 0.03 to 0.2 part by weight of methicone to the mixture are added to the mixture, and 1 to 3 parts by weight of squalane is then added to the mixture including silica and methicone, after which the resultant mixture is agitated with an Agi-mixer or the like, in step (4).

Finally, 5 to 10 parts by weight of a pigment is added and the mixture is agitated for about 20 minutes, in step (5). The pigment used in the step (5) is blended well with a mixer or the like in advance so that the outer color has the same color tone as the inner color.

The steps (2) to (5) are all performed at the room temperature.

After the completion of the steps (1) to (5), the method may further include a filtration process using a 100-mesh filter.

Hereinafter, the present invention will be described more specifically with reference to the following Example and Comparative Examples, which are not intended to limit the scope of the present invention.

Example 1

60 g of silica dimethicone silylate (CAS No. 67762-90-7) is put into a stainless pot and stirred with an Agi-mixer at about 20° C. for about 20 minutes. Then, 640.15 g of DI water (CAS No. 7732-18-5), 10 g of betaine anhydrous (CAS No. 107-43-7), 20 g of arbutin (CAS No. 497-76-7), 0.4 g of adenosine (CAS No. 58-61-7), 10 g of trehalose (CAS No. 99-20-7), 80 g of glycerin (CAS No. 56-81-5), 12.5 g of butylene glycol (CAS No. 107-88-0), 15 g of hydrolyzed collagen (CAS No. 73049-73-7), 0.15 g of phenoxy ethanol (CAS No. 122-99-6), 9.4 g of glycosyl trehalose, 5.4 g of hydrogenated starch hydrolysate (CAS No. 68425-17-2), and 2 g of methylparaben (CAS No. 99-76-3) are put into a separate stainless pot and mixed well together using an Agi-mixer at about 20° C. to prepare a complete solution. This solution is slowly added into the stainless pot containing the stirred silica methicone silylate. The mixture is then stirred with an Agi-mixer at about 20° C. so that the dissolved components are sufficiently impregnated with the silica dimethicone silylate. Subsequently, 29.1 g of silica (CAS No. 7631-86-9) and 0.9 g of methicone (CAS No. 9004-73-3) are put into the pot containing the mixture, and 20 g of squalane (CAS No. 111-01-3) is then added. The resultant mixture is sufficiently stirred at about 20° C. with an Agi-mixer. Then, pigments (15 g of TiO$_2$ AS, 25 g of I.O.Y 3AS, 15 g of I.O.R 3AS, and 20 g of I.O.B 3AS) are added, and the resultant mixture is sufficiently stirred with an Agi-mixer at about 20° C. to prepare a powder essence composition.

Comparative Example 1: Excluding Glycerin 60 g of silica dimethicone silylate (CAS No. 67762-90-7) is put into a stainless pot and stirred with an Agi-mixer at about 20° C. for about 20 minutes. Then, 640.15 g of DI water (CAS No. 7732-18-5), 10 g of betaine anhydrous (CAS No. 107-43-7), 20 g of arbutin (CAS No. 497-76-7), 0.4 g of adenosine (CAS No. 58-61-7), 10 g of trehalose (CAS No. 99-20-7), 12.5 g of butylene glycol (CAS No. 107-88-0), 15 g of hydrolyzed collagen (CAS No. 73049-73-7), 0.15 g of phenoxy ethanol (CAS No. 122-99-6), 9.4 g of glycosyl trehalose, 5.4 g of hydrogenated starch hydrolysate (CAS No. 68425-17-2), and 2 g of methylparaben (CAS No. 99-76-3) are put into a separate stainless pot and mixed well together using an Agi-mixer at about 20° C. to prepare a complete solution. This solution is slowly added into the stainless pot containing the stirred silica methicone silylate. The mixture is then stirred with an Agi-mixer at about 20° C. so that the dissolved components are sufficiently impregnated with the silica dimethicone silylate. Subsequently, 29.1 g of silica (CAS No. 7631-86-9) and 0.9 g of methicone (CAS No. 9004-73-3) are put into the pot containing the mixture, and 20 g of squalane (CAS No. 111-01-3) is then added. The resultant mixture is sufficiently stirred at about 20° C. with an Agi-mixer. Then, pigments (15 g of TiO$_2$ AS, 25 g of I.O.Y 3AS, 15 g of I.O.R 3AS, and 20 g of I.O.B 3AS) are added, and the resultant mixture is sufficiently stirred with an Agi-mixer at about 20° C. to prepare a powder essence composition.

Comparative Example 2: Excluding Methicone 60 g of silica dimethicone silylate (CAS No. 67762-90-7) is put into a stainless pot and stirred with an Agi-mixer at about 20° C. for about 20 minutes. Then, 640.15 g of DI water (CAS No. 7732-18-5), 10 g of betaine anhydrous (CAS No. 107-43-7), 20 g of arbutin (CAS No. 497-76-7), 0.4 g of adenosine (CAS No. 58-61-7), 10 g of trehalose (CAS No. 99-20-7), 80 g of glycerin (CAS No. 56-81-5), 12.5 g of butylene glycol (CAS No. 107-88-0), 15 g of hydrolyzed collagen (CAS No. 73049-73-7), 0.15 g of phenoxy ethanol (CAS No. 122-99-6), 9.4 g of glycosyl trehalose, 5.4 g of hydrogenated starch hydrolysate (CAS No. 68425-17-2), and 2 g of methylparaben (CAS No. 99-76-3) are put into a separate stainless pot and mixed well together using an Agi-mixer at about 20° C. to prepare a complete solution. This solution is slowly added into the stainless pot containing the stirred silica methicone silylate. The mixture is then stirred with an Agi-mixer at about 20° C. so that the dissolved components are sufficiently impregnated with the silica dimethicone silylate. Subsequently, 29.1 g of silica (CAS No. 7631-86-9) is put into the pot containing the mixture, and 20 g of squalane (CAS No. 111-01-3) is then added. The resultant mixture is sufficiently stirred at about 20° C. with an Agi-mixer. Then, pigments (15 g of TiO$_2$ AS, 25 g of I.O.Y 3AS, 15 g of I.O.R 3AS, and 20 g of I.O.B 3AS) are added, and the resultant mixture is sufficiently stirred with an Agi-mixer at about 20° C. to prepare a powder essence composition.

Comparative Example 3: Excluding Squalane 60 g of silica dimethicone silylate (CAS No. 67762-90-7) is put into a stainless pot and stirred with an Agi-mixer at about 20° C. for about 20 minutes. Then, 640.15 g of DI water (CAS No. 7732-18-5), 10 g of betaine anhydrous (CAS No. 107-43-7), 20 g of arbutin (CAS No. 497-76-7), 0.4 g of adenosine (CAS No. 58-61-7), 10 g of trehalose (CAS No. 99-20-7), 80 g of glycerin (CAS No. 56-81-5), 12.5 g of butylene glycol (CAS No. 107-88-0), 15 g of hydrolyzed collagen (CAS No. 73049-73-7), 0.15 g of phenoxy ethanol (CAS No. 122-99-6), 9.4 g of glycosyl trehalose, 5.4 g of hydrogenated starch hydrolysate (CAS No. 68425-17-2), and 2 g of methylparaben (CAS No. 99-76-3) are put into a separate stainless pot and mixed well together using an Agi-mixer at about 20° C. to prepare a complete solution. This solution is slowly added into the stainless pot containing the stirred silica methicone silylate. The mixture is then stirred with an Agi-mixer at about 20° C. so that the dissolved components are sufficiently impregnated with the silica dimethicone silylate. Subsequently, 29.1 g of silica (CAS No. 7631-86-9) and 0.9 g of methicone (CAS No. 9004-73-3) are put into the pot containing the mixture. Then, pigments (15 g of TiO$_2$ AS, 25 g of I.O.Y 3AS, 15 g of I.O.R 3AS, and 20 g of I.O.B 3AS) are added, and the resultant mixture is sufficiently stirred with an Agi-mixer at about 20° C. to prepare a powder essence composition.

The powder essence compositions prepared in Example 1 and Comparative Examples 1, 2 and 3 are evaluated according to the following performance testing.

The following experiments involve five female volunteers aged 21 to 30 years old (specimens 1 to 5) and another five female volunteers aged 31 to 40 years old (specimens 6 to 10), who are all wearing no facial makeup. Each female volunteer cleanses her face one time with warm water and a cleanser and, in 30 minutes, applies the composition of the present invention to the lip and cheek in an amount of 1 g (lip) and 3 g (cheek), respectively. The application of the compositions according to Example 1 and Comparative Examples 1, 2 and 3 is conducted daily for 4 days. The daily application of the powder essence is conducted at round 8 a.m., and the volunteers are allowed to have their own daily routine during the experiments. The volunteers have no idea about which specimens correspond to the Example or Comparative Examples, and they have the option of deciding the application order of the powder essence compositions so that the powder essence compositions are tested at random. Each volunteer has a survey paper to record the score for each test item at a given time.

[Coloring Testing]

Each powder essence composition according to Example 1 or Comparative Examples 1, 2 and 3 is applied to the skin of lip and cheek. A visual inspection is then performed to evaluate the composition's color intensity, which is scored on the scale of 1 to 5 (5 is excellent; 4 is good; 3 is fair; 2 is poor; 1 is very poor). The evaluation results are presented in Tables 1 to 8.

[Skin Feeling Testing—Sensory Inspection]

Ten female volunteers are recruited to apply each powder essence composition according to Example 1 or Comparative Examples 1, 2 and 3 to the skin of lips and cheeks and conduct the sensory inspection in regards to the skin feeling. In the sensory inspection, the skin feeling is classified into three categories: (1) skin feeling during application (the softness the skin feels during application); (2) skin feeling immediately after application (the light feeling of the powder essence applied to the cheeks and lips); and (3) skin feeling in daily routine after application (the freshness from the powder essence applied to the cheeks and lips). The skin feel is scored on the scale of 1 to 5, thus 5 is excellent; 4 is good; 3 is fair; 2 is poor; 1 is very poor. The evaluation results are presented in Tables 1 to 8.

[Color Retention Testing—Sensory Inspection]

The volunteers are recruited to apply each powder essence composition according to Example 1 or Comparative Examples 1, 2 and 3 to the skin of lips and cheeks at 8 a.m. and record the evaluation on the retention of the original color intensity in 4 hours (at noon), 7 hours (at 3 p.m.), 10 hours (at 6 p.m.), and 12 hours (at 8 p.m.) after the application. The color retention is scored on the scale of 1 to 5 according to the change of the color intensity: thus, 5 is no change of the color intensity; 4 is an insignificant deterioration of color intensity that does not affect the aesthetic impression; 3 is a slight deterioration of color intensity that does not affect the aesthetic impression; 2 is a significant deterioration of color intensity; 1 is almost no color as before application. The evaluation results are presented in Tables 1 to 8.

TABLE 1

Application area: Cheeks

| Example | Specimen | Coloring | Skin feel During application | Skin feel Right after application | Skin feel Daily routine | Color retention 4 hr | Color retention 7 hr | Color retention 10 hr | Color retention 12 hr |
|---|---|---|---|---|---|---|---|---|---|
| 1 | 1 | 5 | 5 | 5 | 5 | 5 | 5 | 5 | 4 |
| 1 | 2 | 4 | 4 | 5 | 4 | 5 | 5 | 5 | 5 |
| 1 | 3 | 5 | 5 | 4 | 5 | 5 | 5 | 5 | 4 |
| 1 | 4 | 5 | 5 | 5 | 5 | 5 | 5 | 5 | 5 |
| 1 | 5 | 5 | 5 | 4 | 5 | 5 | 4 | 4 | 4 |
| 1 | 6 | 5 | 4 | 5 | 4 | 5 | 5 | 4 | 4 |
| 1 | 7 | 5 | 5 | 4 | 5 | 5 | 4 | 4 | 4 |
| 1 | 8 | 4 | 5 | 5 | 5 | 5 | 5 | 5 | 5 |
| 1 | 9 | 4 | 4 | 5 | 5 | 5 | 5 | 5 | 5 |
| 1 | 10 | 5 | 5 | 5 | 4 | 5 | 5 | 5 | 4 |

TABLE 2

Application area: Lips

| Example | Specimen | Coloring | Skin feel During application | Skin feel Right after application | Skin feel Daily routine | Color retention 4 hr | Color retention 7 hr | Color retention 10 hr | Color retention 12 hr |
|---|---|---|---|---|---|---|---|---|---|
| 1 | 1 | 5 | 5 | 5 | 5 | 5 | 5 | 5 | 5 |
| 1 | 2 | 4 | 4 | 5 | 4 | 5 | 5 | 5 | 5 |
| 1 | 3 | 5 | 5 | 4 | 4 | 5 | 5 | 5 | 4 |
| 1 | 4 | 5 | 4 | 5 | 5 | 5 | 5 | 4 | 5 |
| 1 | 5 | 5 | 5 | 4 | 5 | 5 | 4 | 4 | 4 |
| 1 | 6 | 4 | 4 | 5 | 4 | 5 | 5 | 5 | 5 |
| 1 | 7 | 5 | 5 | 5 | 5 | 5 | 5 | 4 | 4 |
| 1 | 8 | 5 | 5 | 5 | 4 | 5 | 5 | 5 | 5 |
| 1 | 9 | 4 | 5 | 5 | 5 | 5 | 5 | 5 | 5 |
| 1 | 10 | 5 | 5 | 5 | 4 | 5 | 5 | 5 | 5 |

TABLE 3

Application area: Cheeks

| Comparative Example | Specimen | Coloring | Skin feel During application | Skin feel Right after application | Skin feel Daily routine | Color retention 4 hr | Color retention 7 hr | Color retention 10 hr | Color retention 12 hr |
|---|---|---|---|---|---|---|---|---|---|
| 1 | 1 | 3 | 2 | 3 | 3 | 4 | 3 | 2 | 1 |
| 1 | 2 | 2 | 3 | 3 | 2 | 4 | 4 | 3 | 1 |
| 1 | 3 | 3 | 2 | 3 | 2 | 3 | 3 | 2 | 1 |
| 1 | 4 | 2 | 3 | 3 | 3 | 4 | 3 | 2 | 2 |
| 1 | 5 | 3 | 3 | 2 | 2 | 3 | 3 | 2 | 1 |
| 1 | 6 | 2 | 2 | 3 | 2 | 4 | 3 | 3 | 1 |
| 1 | 7 | 2 | 3 | 3 | 2 | 4 | 3 | 1 | 2 |
| 1 | 8 | 3 | 3 | 3 | 2 | 3 | 2 | 2 | 1 |
| 1 | 9 | 3 | 2 | 2 | 3 | 5 | 3 | 2 | 1 |
| 1 | 10 | 2 | 3 | 3 | 2 | 4 | 2 | 2 | 1 |

TABLE 4

Application area: Lips

| Comparative Example | Specimen | Coloring | Skin feel During application | Skin feel Right after application | Daily routine | Color retention 4 hr | 7 hr | 10 hr | 12 hr |
|---|---|---|---|---|---|---|---|---|---|
| 1 1 |  | 2 | 2 | 3 | 2 | 4 | 3 | 2 | 1 |
| 1 2 |  | 2 | 3 | 3 | 3 | 4 | 3 | 3 | 1 |
| 1 3 |  | 3 | 2 | 2 | 2 | 3 | 3 | 1 | 1 |
| 1 4 |  | 3 | 3 | 3 | 3 | 4 | 3 | 2 | 2 |
| 1 5 |  | 3 | 3 | 2 | 2 | 3 | 2 | 2 | 1 |
| 1 6 |  | 2 | 2 | 3 | 3 | 4 | 3 | 3 | 1 |
| 1 7 |  | 2 | 3 | 3 | 2 | 3 | 3 | 2 | 2 |
| 1 8 |  | 3 | 3 | 3 | 2 | 3 | 2 | 2 | 1 |
| 1 9 |  | 2 | 2 | 2 | 3 | 4 | 3 | 1 | 1 |
| 1 10 |  | 2 | 3 | 3 | 2 | 4 | 2 | 2 | 1 |

TABLE 5

Application area: Cheeks

| Comparative Example | Specimen | Coloring | Skin feel During application | Skin feel Right after application | Daily routine | Color retention 4 hr | 7 hr | 10 hr | 12 hr |
|---|---|---|---|---|---|---|---|---|---|
| 2 1 |  | 2 | 3 | 3 | 3 | 4 | 3 | 2 | 1 |
| 2 2 |  | 2 | 3 | 2 | 2 | 3 | 3 | 2 | 1 |
| 2 3 |  | 3 | 2 | 3 | 2 | 3 | 3 | 2 | 1 |
| 2 4 |  | 2 | 3 | 2 | 3 | 4 | 3 | 2 | 2 |
| 2 5 |  | 3 | 2 | 2 | 2 | 3 | 3 | 2 | 1 |
| 2 6 |  | 3 | 2 | 3 | 3 | 4 | 3 | 3 | 1 |
| 2 7 |  | 2 | 3 | 3 | 2 | 4 | 3 | 2 | 2 |
| 2 8 |  | 3 | 2 | 3 | 2 | 3 | 2 | 2 | 1 |
| 2 9 |  | 3 | 2 | 2 | 3 | 4 | 3 | 2 | 1 |
| 2 10 |  | 2 | 3 | 3 | 2 | 3 | 2 | 2 | 1 |

TABLE 6

Application area: Lips

| Comparative Example | Specimen | Coloring | Skin feel During application | Skin feel Right after application | Daily routine | Color retention 4 hr | 7 hr | 10 hr | 12 hr |
|---|---|---|---|---|---|---|---|---|---|
| 2 1 |  | 2 | 2 | 3 | 2 | 4 | 3 | 2 | 2 |
| 2 2 |  | 2 | 3 | 3 | 3 | 4 | 3 | 2 | 1 |
| 2 3 |  | 3 | 2 | 3 | 2 | 3 | 3 | 1 | 1 |
| 2 4 |  | 3 | 3 | 3 | 3 | 4 | 3 | 2 | 2 |
| 2 5 |  | 2 | 2 | 2 | 2 | 3 | 2 | 2 | 1 |
| 2 6 |  | 2 | 2 | 3 | 3 | 4 | 3 | 2 | 1 |
| 2 7 |  | 3 | 3 | 3 | 3 | 3 | 3 | 2 | 2 |
| 2 8 |  | 2 | 3 | 3 | 2 | 3 | 2 | 2 | 1 |
| 2 9 |  | 2 | 2 | 2 | 3 | 3 | 3 | 1 | 1 |
| 2 10 |  | 2 | 3 | 3 | 2 | 4 | 2 | 2 | 1 |

TABLE 7

Application area: Cheeks

| Comparative Example | Specimen | Coloring | Skin feel During application | Skin feel Right after application | Daily routine | Color retention 4 hr | 7 hr | 10 hr | 12 hr |
|---|---|---|---|---|---|---|---|---|---|
| 3 1 |  | 3 | 3 | 3 | 3 | 4 | 3 | 2 | 1 |
| 3 2 |  | 2 | 3 | 2 | 2 | 4 | 4 | 3 | 1 |
| 3 3 |  | 3 | 2 | 3 | 2 | 3 | 3 | 2 | 1 |
| 3 4 |  | 2 | 3 | 3 | 3 | 4 | 3 | 2 | 2 |
| 3 5 |  | 3 | 3 | 2 | 2 | 3 | 3 | 2 | 1 |
| 3 6 |  | 2 | 2 | 3 | 2 | 4 | 2 | 2 | 1 |
| 3 7 |  | 3 | 2 | 2 | 2 | 4 | 3 | 2 | 2 |
| 3 8 |  | 3 | 3 | 3 | 2 | 3 | 2 | 2 | 1 |
| 3 9 |  | 3 | 2 | 2 | 3 | 4 | 3 | 2 | 2 |
| 3 10 |  | 2 | 3 | 3 | 2 | 4 | 2 | 2 | 1 |

TABLE 8

Application area: Lips

| Comparative Example | Specimen | Coloring | Skin feel During application | Skin feel Right after application | Daily routine | Color retention 4 hr | 7 hr | 10 hr | 12 hr |
|---|---|---|---|---|---|---|---|---|---|
| 3 1 |  | 3 | 2 | 3 | 2 | 3 | 3 | 2 | 2 |
| 3 2 |  | 2 | 3 | 3 | 3 | 4 | 3 | 3 | 1 |
| 3 3 |  | 3 | 2 | 3 | 2 | 3 | 3 | 1 | 1 |
| 3 4 |  | 3 | 3 | 3 | 3 | 4 | 3 | 2 | 2 |
| 3 5 |  | 3 | 3 | 2 | 2 | 3 | 2 | 2 | 1 |
| 3 6 |  | 2 | 2 | 3 | 3 | 4 | 3 | 3 | 1 |
| 3 7 |  | 3 | 3 | 3 | 3 | 3 | 2 | 2 | 2 |
| 3 8 |  | 3 | 3 | 3 | 2 | 3 | 2 | 2 | 1 |
| 3 9 |  | 2 | 2 | 2 | 2 | 4 | 3 | 2 | 1 |
| 3 10 |  | 3 | 3 | 3 | 2 | 4 | 2 | 2 | 2 |

As can be seen from the results of Tables 1 to 8, the composition of Example 1 according to one embodiment of the present invention was far superior to the compositions of Comparative Examples 1, 2 and 3 in regards to the coloring, skin feeling and color retention.

[Skin Toxicity Testing]

The ten female volunteers were recruited to participate in the skin toxicity testing of the powder essence composition of the present invention as prepared in Example 1. Skin toxicity is determined in two ways: (1) taking the survey on the skin irritation on the application area during the testing; and (2) recruiting the volunteers to clean their face in 12 hours after the completion of the color retention testing, apply the powder essence composition to the cheeks and lips and visually examine whether it causes skin problems such as rash or the like on the application areas, that is, cheeks and lips. The evaluation results are presented in Table 9.

TABLE 9

Skin toxicity testing

| Example | Specimen | Test item Irritation | Rash | Other skin problems |
|---|---|---|---|---|
| 1 | 1 | No | No | No |
| 1 | 2 | No | No | No |

TABLE 9-continued

Skin toxicity testing

| Example | Specimen | Test item | | Other skin problems |
|---|---|---|---|---|
| | | Irritation | Rash | |
| 1 | 3 | No | No | No |
| 1 | 4 | No | No | No |
| 1 | 5 | No | No | No |
| 1 | 6 | No | No | No |
| 1 | 7 | No | No | No |
| 1 | 8 | No | No | No |
| 1 | 9 | No | No | No |
| 1 | 10 | No | No | No |

Referring to Table 9, the powder essence composition of the present invention causes no skin problem, such as irritation, rash, etc., in all the volunteers of the experiment. This study backs up the stability of the powder essence composition of the present invention.

What is claimed is:

1. A long-lasting powder essence composition with improved coloring and skin feeling, the composition comprising 5 to 7 parts by weight of silica dimethicone silylate, 50 to 80 parts by weight of water, 1 to 10 parts by weight of glycerine, 0.001 to 0.003 part by weight of phenoxy ethanol, 0.5 to 3 parts by weight of glycosyl trehalose, 0.3 to 2 parts by weight of hydrogenated starch hydrolysate, 0.1 to 0.5 part by weight of methylparaben, 1 to 5 parts by weight of silica, 0.03 to 0.2 part by weight of methicone, 1 to 3 parts by weight of squalane, and 5 to 10 parts by weight of a pigment.

2. The long-lasting powder essence composition with improved coloring and skin feeling as claimed in claim 1, wherein the composition further comprises 1 to 5 parts by weight of betaine, 1 to 5 parts by weight of arbutin, 0.01 to 0.1 part by weight of adenosine, and 0.5 to 5 parts by weight of trehalose.

3. The long-lasting powder essence composition with improved coloring and skin feeling as claimed in claim 1, wherein the composition further comprises 1 to 3 parts by weight of butylene glycol and 1 to 3 parts by weight of hydrolyzed collagen.

4. A method for preparing a long-lasting powder essence composition with improved coloring and skin feeling, the method comprising:

(1) adding 5 to 7 parts by weight of silica dimethicone silylate to a preparation container and stirring;

(2) adding 50 to 80 parts by weight of water, 1 to 10 parts by weight of glycerine, 0.001 to 0.003 part by weight of phenoxy ethanol, 0.5 to 3 parts by weight of glycosyl trehalose, 0.3 to 2 parts by weight of hydrogenated starch hydrolysate, and 0.1 to 0.5 part by weight of methylparaben, and dissolving under agitation to prepare a solution;

(3) sufficiently mixing the solution with the stirred silica dimethicone silylate so that the solution is impregnated with the silica dimethicone silylate, thereby preparing a mixture;

(4) adding 1 to 5 parts by weight of silica and 0.03 to 0.2 part by weight of methicone to the mixture, adding 1 to 3 parts by weight of squalane to the mixture including silica and methicone, and stirring; and (5) adding 5 to 10 parts by weight of a pigment and stirring.

5. The method as claimed in claim 4, wherein the step (2) further includes adding 1 to 5 parts by weight of betaine, 1 to 5 parts by weight of arbutin, 0.01 to 0.1 part by weight of adenosine, 0.5 to 5 parts by weight of trehalose, 1 to 3 parts by weight of butylene glycol, and 1 to 3 parts by weight of hydrolyzed collagen, and dissolving under agitation.

* * * * *